United States Patent [19]

Coates et al.

[11] Patent Number: 5,100,409
[45] Date of Patent: Mar. 31, 1992

[54] SHAPING AND TRIAL REDUCTION GUIDE FOR IMPLANTATION OF FEMORAL PROSTHESIS AND METHOD OF USING SAME

[75] Inventors: Bradley J. Coates, Cordova, Tenn.; Leo A. Whiteside, Chesterfield, Mo.

[73] Assignee: Dow Corning Wright Corporation, Arlington, Tenn.

[21] Appl. No.: 666,160

[22] Filed: Mar. 7, 1991

[51] Int. Cl.⁵ .................... A61F 2/46; A61F 2/38 A61F 2/38
[52] U.S. Cl. .................... 606/88; 606/87; 623/20
[58] Field of Search .................... 606/86–88; 623/20, 18

[56] References Cited

U.S. PATENT DOCUMENTS

| | | | |
|---|---|---|---|
| 4,474,177 | 10/1984 | Whiteside | 606/88 |
| 4,568,348 | 2/1986 | Johnson et al. | 623/20 |
| 4,721,104 | 1/1988 | Kaufman et al. | 606/88 |
| 5,035,699 | 7/1991 | Coates | 606/86 |

FOREIGN PATENT DOCUMENTS 0376658 7/1990 European Pat. Off. .............. 623/20

Primary Examiner—Randall L. Green
Assistant Examiner—D. Willse
Attorney, Agent, or Firm—John L. Chiatalas

[57] ABSTRACT

According to the invention, there is provided a trial implant comprising a modular bracket defining a structure having an internal surface adapted to be seated on the distal aspect of a resected femur bone and an external surface with a shape resembling the normal distal condyle of the femur. The bracket has an elongated central opening appointed to expose the resected bone of the femur, including a pair of tracks for guiding a tool along a predetermined path for controlled shaping of a patellar groove in the bone exposed through the opening. A replaceable insert covers the opening and articulates with a proximal aspect of the tibia during interoperative trial reduction of the knee joint, whereby prior removal of the bracket from the resected bone is unnecessary following shaping of the patellar groove. Preferably, the insert and guide tracks cooperate together to securely position the insert within the opening during trial reduction. A surgical method is also provided using the described trial implant guide.

5 Claims, 4 Drawing Sheets

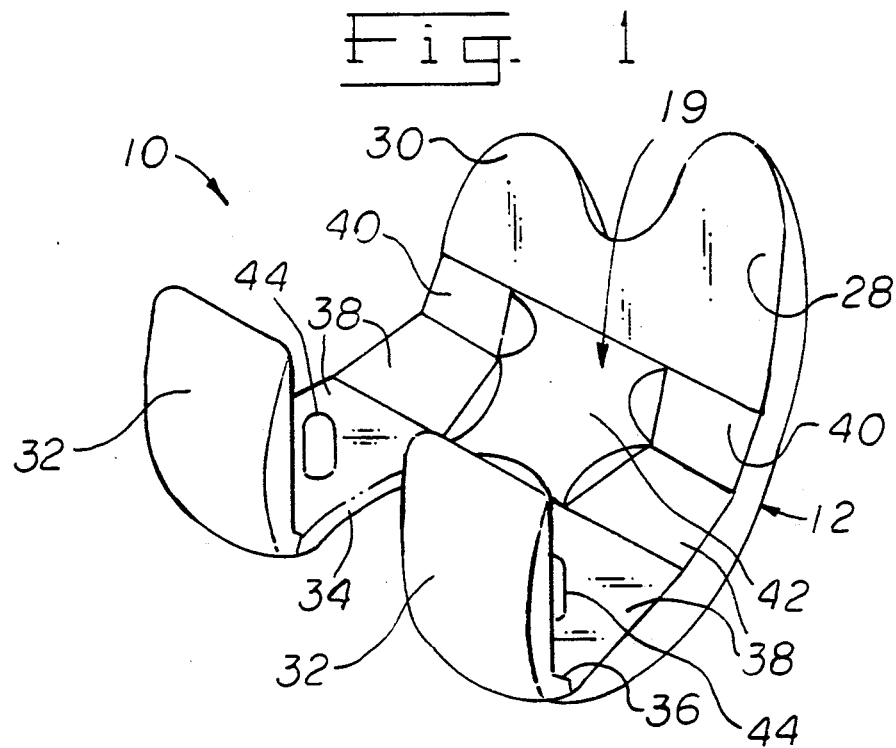
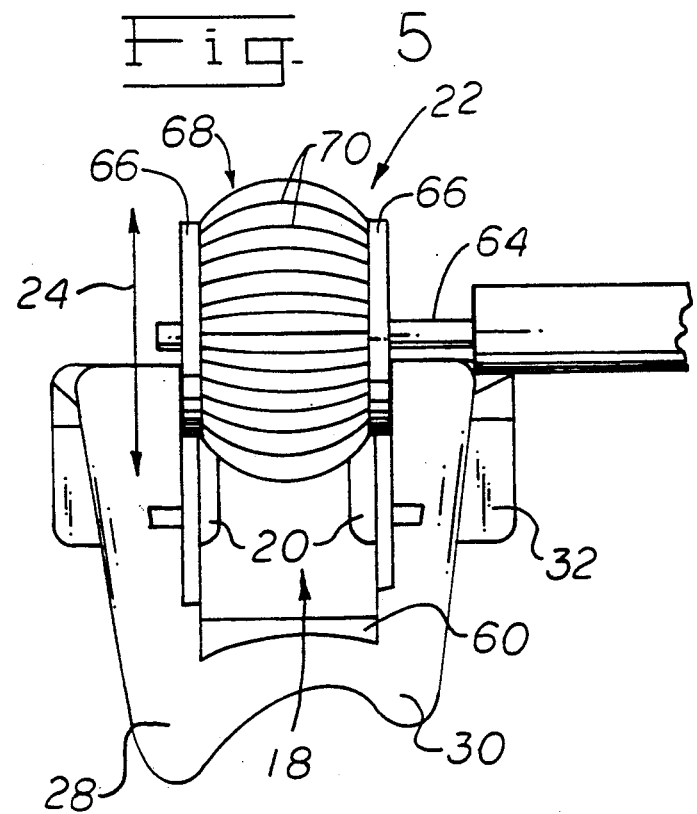

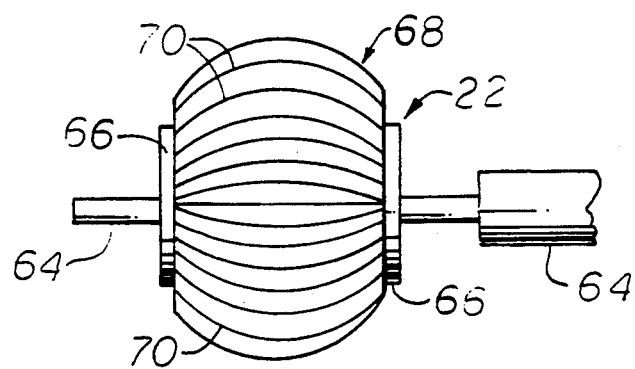
Fig. 4
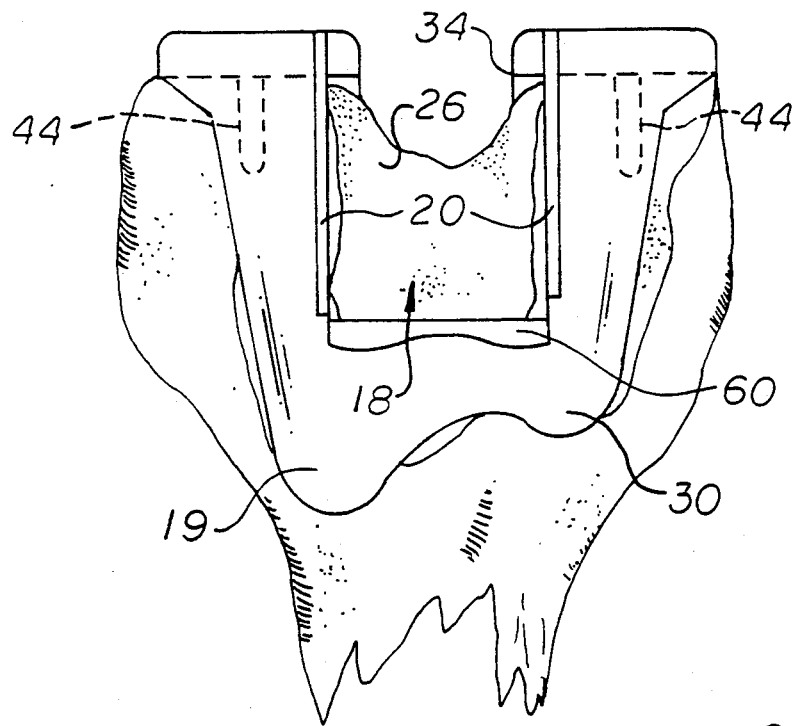
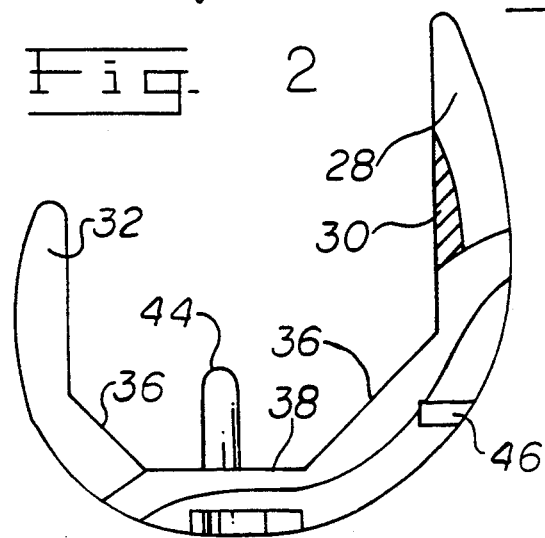
Fig. 2

SHAPING AND TRIAL REDUCTION GUIDE FOR IMPLANTATION OF FEMORAL PROSTHESIS AND METHOD OF USING SAME

TECHNICAL FIELD

This invention generally concerns orthopedic surgical devices, particularly instrumentation used in preparing a distal femoral bone surface to receive a condylar prosthesis, as well as a method of using such instrumentation.

BACKGROUND OF THE INVENTION

During surgical implantation of femoral condylar prostheses, it is typically necessary to utilize some type of tool to gauge whether or not the distal aspect of the femur has been properly sized to receive the condylar implant. This gauge typically resembles the actual prosthesis which will be implanted. The surgeon first "resects" the surface of the bone to match the geometry of the implant by making several cuts as shown, for example, in U.S. Pat. No. 4,474,177 to Whiteside, the entire disclosure of which is expressly incorporated by reference herein and relied upon.

Once the distal aspect of the femur has been resected, a convex patellar groove is formed in the anterior surface of the resected bone, in order to accommodate the mating concave patellar track of the condylar implant. The external distal surface of the condylar implant, particularly that of the patellar track, articulates with the proximal aspect of the tibia, which is also resected to receive a tibial implant in a total knee replacement. The present inventors have previously devised a cutting guide for shaping the patellar groove in allowed U.S. patent application Ser. No. 462,268, filed Jan. 9, 1990, the entire disclosure of which is expressly incorporated by reference herein and relied upon. Depending upon the degree of knee reconstruction indicated, a patellar prosthesis may also be implanted as shown, for example, in U.S. patent application Ser. No. 466,093, filed Jan. 12, 1990 in the name of the instant inventors, the entire disclosure of which is expressly incorporated by reference herein and relied upon.

A challenge confronted by condylar implant systems is the need to both accurately form a patellar groove in the resected surface of the distal femur and perform a trial reduction of the knee joint to ascertain proper sizing of the condylar implant. This is conventionally a sequential procedure employing first a guide seated on the resected bone for engaging a shaping tool which forms the patellar groove in the bone. Secondly, a trial condylar implant is seated on the resected surface of the distal femur, having a size and shape resembling that of the permanent condylar prosthesis actually being implanted, after which the trial reduction of the knee is performed by articulating the femur and tibia. Following satisfactory trial reduction, the trial implant is removed and replaced by the permanent condylar implant. A disadvantage of the procedure set forth above is degradation of the bone caused by alternate insertion and removal of separate track cutting and trial implant guides, respectively. Moreover, use of separate track cutting and trial implant guides is relatively inefficient and time-consuming, further complicating the surgical procedure for reconstructing the knee joint.

Accordingly, there is a need for a device and method which combine the features of a femoral trial implant and patellar track cutting guide, so that the patellar groove may be shaped and a surgical trial reduction accurately performed using the same instrumentation.

SUMMARY OF THE INVENTION AND ADVANTAGES

According to the invention, there is provided a trial implant comprising a modular bracket defining a structure having an internal surface adapted to be seated on the distal aspect of a resected femur bone and an external surface with a shape resembling the normal distal condyle of the femur. The bracket has an elongated central opening appointed to expose the resected surface of the femur, including means for guiding a tool along a predetermined path for controlled shaping of a patellar groove in the surface exposed through the opening. A replaceable insert covers the opening and articulates with a proximal aspect of the tibia for interoperative trial reduction of the knee joint, whereby prior removal of the bracket from the resected bone is unnecessary following shaping of the patellar groove.

In a preferred embodiment, the guide means of the invention further comprises a track extending along a side of the opening for engaging the shaping tool.

In another preferred embodiment, the track comprises a pair of rails which engage and align the insert within the opening during trial reduction.

In still another preferred embodiment, means are provided for securely connecting the insert with the guide means.

According to the invention, a method of implanting a condylar prosthesis onto the proximal aspect of a resected femur comprises the steps of resecting the distal aspect of the femur to receive a trial implant thereon. The trial implant provided comprises a bracket defining a modular structure having an internal surface adapted to be seated on the distal aspect of the femur and an external surface formed with a shape resembling the normal distal condyle, including an elongated central opening appointed to expose an anterior distal resected surface of the femur to a shaping tool. The method further comprises the step of providing means for guiding the tool along a predetermined path for controlled shaping of the anterior distal surface exposed through the opening. A shaping tool is then moved along the path, cutting or abrading a patellar groove in the bone. An insert having a corresponding shape is brought into secure engagement with the opening, covering the patellar groove. The seated bracket, with the insert covering the opening, functions as a trial implant as the femur and tibia are articulated during a trial reduction of the total knee joint.

An advantage of this invention is a device and method of using the device by which a patellar groove may be shaped in a resected femur by instrumentation which also functions as a trial condylar implant during trial reduction of the total knee joint.

Another advantage of this invention is a method and a device by which excessive wear on the distal aspect of the femur is avoided by replacing the use of multiple instruments with a single modular device.

BRIEF DESCRIPTION OF THE DRAWINGS

The above and other objects and advantages of the present invention will become apparent to those skilled in the art upon an examination of the following Detailed Description and Drawings which are illustrative of the present invention wherein:

FIG. 1 is a internal perspective view of a trial implant according to this invention;

FIG. 2 is a side elevation view of the trial implant of the invention;

FIG. 4 is a frontal view of the modular bracket of the invention seated on the resected distal femur, in combination with a cutting tool being used to shape the patellar groove in the bone;

FIG. 5 is a frontal external view of the bracket, particularly the guide means of the invention in combination with a shaping tool;

DETAILED DESCRIPTION OF ONE OR MORE PREFERRED EMBODIMENTS

Figure 3:
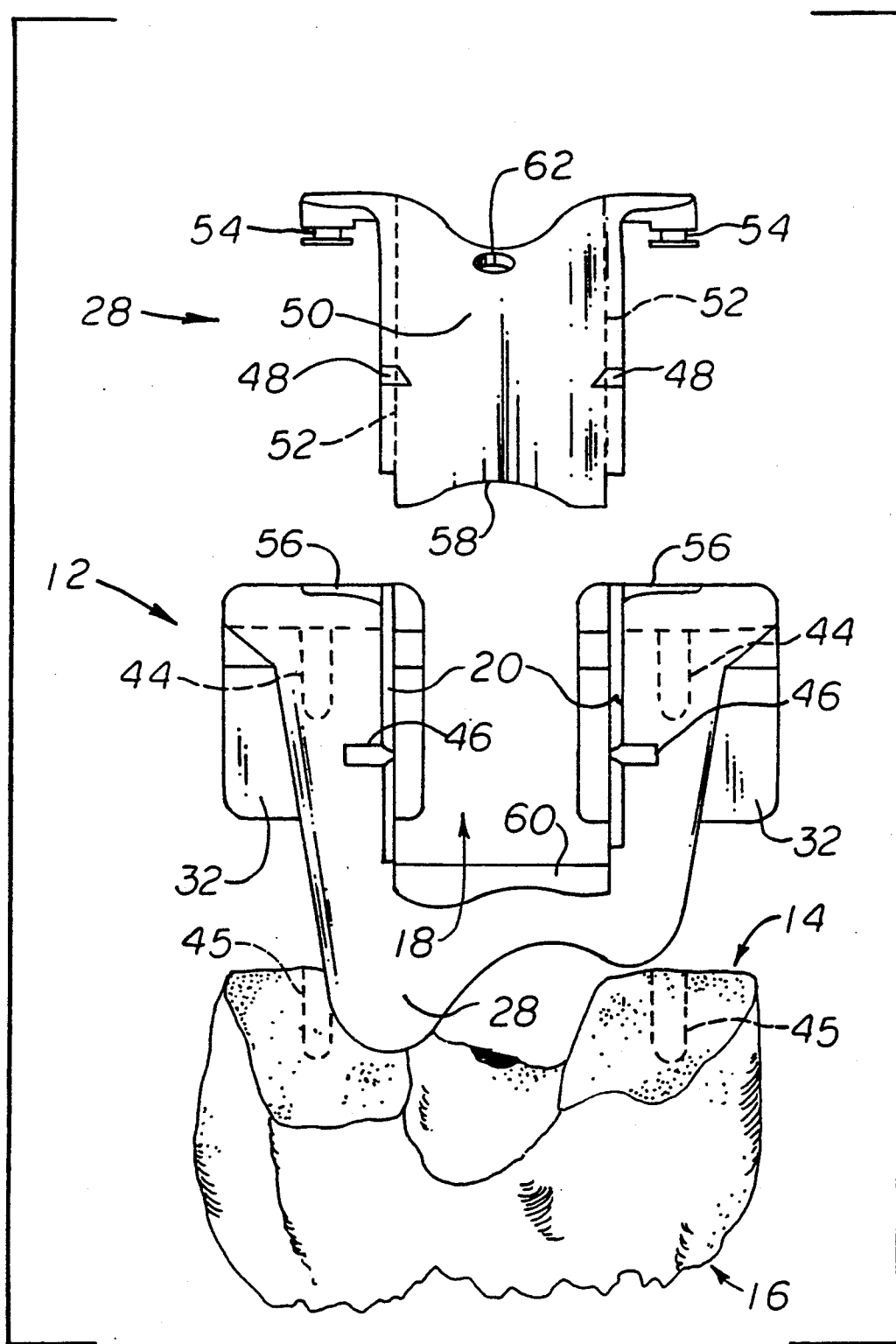
FIG. 3 is an exploded perspective view of the trial implant of the invention, showing the modular bracket being seated on the resected distal femur with the insert removed.
Figure 6:
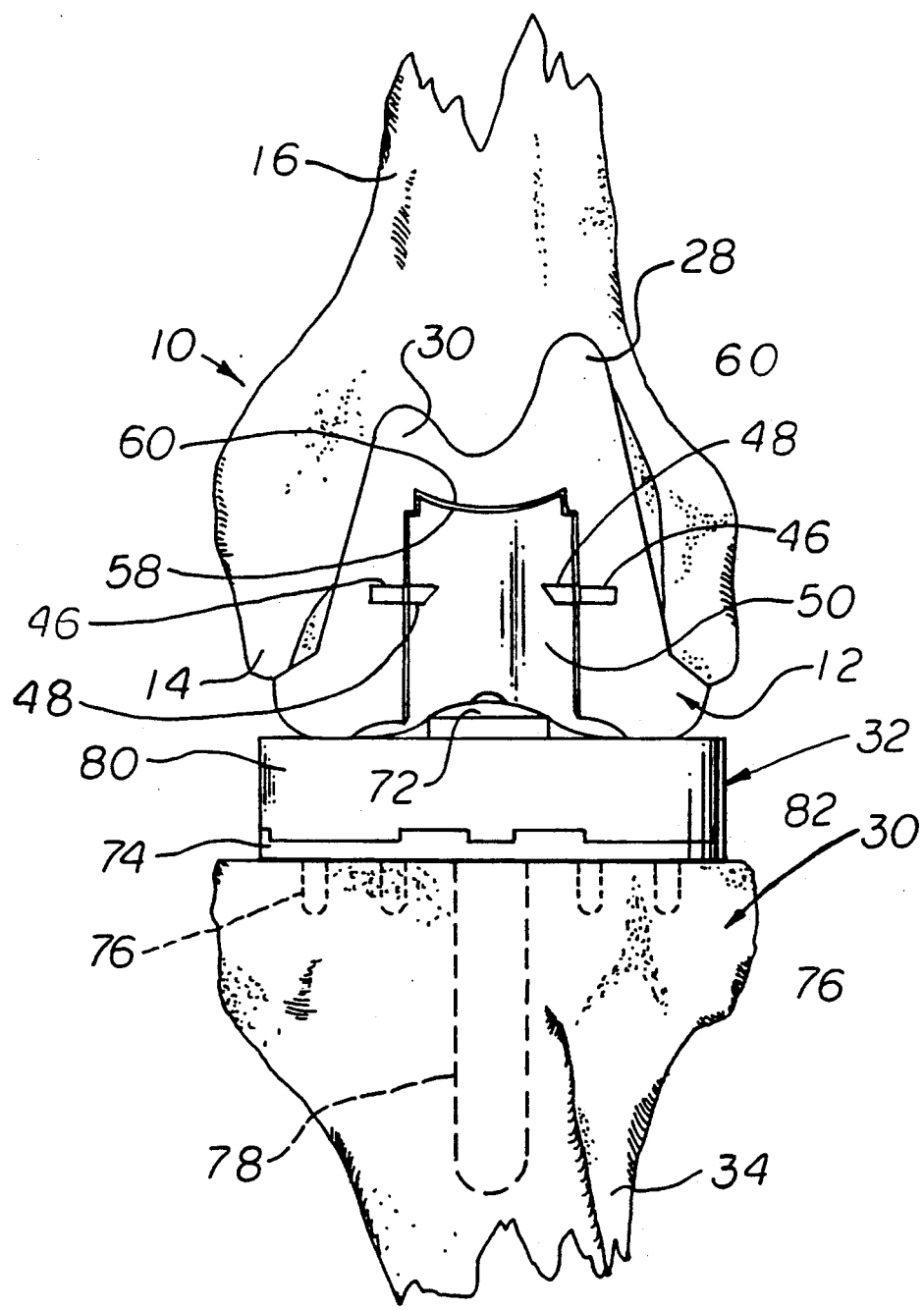
FIG. 6 is an external frontal view of the trial implant, showing the insert securely positioned within the opening of the bracket and articulating with a tibial prosthesis during a trial reduction of the knee joint.

Referring to FIG. 1, a trial implant is generally shown at 10 comprising a modular bracket, generally indicated at 12, defining a structure having an internal surface (facing the viewer) adapted to be seated on a distal aspect, generally indicated at 14, of a resected femur bone, shown at 16 in FIGS. 3, 4 and 6. With particular reference to FIGS. 3, 5 and 4, the bracket has an external surface (facing the viewer) resembling the normal distal condyle of the femur and an elongated central opening, generally indicated at 18 which is appointed to expose the resected distal aspect 14 of the femur 16. Means are provided in the form of parallel tracks or rails 20 for guiding a tool, generally indicated at 22 along a predetermined path in the direction of arrow 24 for controlled shaping of a patellar groove 26 (FIG. 4) in the bone exposed through the opening 18. A replaceable insert, generally indicated at 19 (FIGS. 1 and 3), covers the opening 16 and articulates with either the normal surface or a prosthesis 32 which is implanted on the resected surface of the proximal aspect 30 of the tibia 34 during interoperative trial reduction of the knee joint as shown in FIG. 6.

Referring to the FIG. 1, the internal surface of the trial implant 10 is shown comprising a medial 28 and lateral 30 portions of an anterior condylar flange, a pair of posterior condylar flanges 32 which define an intercondylar notch 34 and a series of planar areas. Specifically, the planar areas comprise a smooth metal finish, since tissue ingrowth into the internal surface of the trial implant 10 is not necessary and, in fact, a non-abrasive action is desirable in seating the trial implant 10 on the resected distal aspect 14 of the femur 16. With additional reference to FIG. 2, the planar surfaces which comprise the internal surface of the trial implant, as shown with the insert 19 positioned in the opening 18 (FIGS. 1-2) include a posterior 36, distal 38 and anterior 40 surface. A humped distal internal contact surface 42 of the trial implant 10, constitutes the internal surface of the insert 19. Likewise, the internal surfaces of the posterior condyles 32 and the medial 28 and lateral 30 portions of the anterior condyle, respectively, also have a smooth metal finish to facilitate onto and off from the resected bone. The cleaner surfaces correspond to the resection cuts made in the distal aspect 14 of the femur 16. A pair of pegs 44 are formed in the planar surface 38 and project into corresponding holes 48, shown in phantom in FIGS. 3 through 4, bored in the distal aspect 14 of the femur 16.

Referring to FIG. 3, the bracket 12 has a pair of alignment notches 46 on opposed sides of opening 18, which align with a pair of corresponding notches 48 formed on opposed sides of the insert 19. The insert 19 further comprises a central concave patellar track 50 and a pair of opposed lateral flanges 52 on either side of the patellar track 50. The lateral flanges 52 engage the rails 20 of the bracket 12. The insert is securely positioned in place on the bracket by a pair of opposed studs 54 which meet with a corresponding pair of apertures 56 formed in the external distal surface of the bracket 12. The insert 19 has an interior shoulder 58 which engages in abutment ledge 60 formed in the interior condyle of the bracket 12. The insert 19 may be readily positioned within the opening 18 of the bracket 12 by means of a gripping aperature 62 formed in the patellar track 50 of the insert 19; likewise, the alignment notches 48 may also facilitate interoperative removal and replacement of the insert within the opening 18 as needed.

Referring to FIG. 4, the shaping tool 22 further comprises a drive shaft 64 rotatably mounted by means of a bearing sleeve 66 to a cutting element, generally indicated at 68, having a plurality of covex-shaped ribs which cut and/or abrade the resected surface of the resected surface of the distal femur to form the patellar groove 26.

Referring to FIG. 5, the bearing sleeve 66 extends outwardly from either side of the cutting element 68 and does not rotate with the cutting element 68. Rather, the bearing sleeve 66 rotates independently of the cutting element 68, engaging and traveling along the rails 20 which establishes the predetermined path indicated by the arrow 24 two shapes of patellar groove.

Once the patellar groove 26 has been formed in the manner describerd above, the insert is replaced into the opening 18 and the knee joint is relocated, as shown in FIG. 6 where the proximal aspect 30 of the tibia 34 has also been resected and a prosthesis 32 implanted, so that the articulating process of the tibial implant engages the patellar track 50 of the condylar prosthesis. The tibial prosthesis 32 may be selected from any of a variety of conventional types available to those skilled in the art. The tibial prosthesis 32 preferably comprises a metal base plate 74 which is implanted into the resected proximal aspect 30 of the tibia 34 by means of pairs of lateral pegs, shown in phantom at 76 and a central long stem 78 which is fit into the intermedullary canal of the tibia 34. The tibial implant 32 is of modular construction, further comprising an upper articulating portion 80, preferably formed of a hard plastic material, for example, high molecular weight polyethylene, to provide a no-degrading articulating surface. The upper portion 80 locks into place within the base 74 by means of an arrangement of notches 82 and the upper portion may be replaced when worn without removing the metal base portion 74 implanted into the bone.

These and other variations of the present invention may be made which fall within the scope of the appended claims even though such variations were not specifically discussed above.

That which is claimed is:

1. A femoral trial implant comprising:
   (a) a modular bracket defining a structure having an internal surface adapted to be seated on the distal aspect of a resected femur and an external surface with a shape partially resembling the normal distal condyle of the femur, including an elongagted central opening adapted to expose a selected portion of the anterior distal resected surface of the femur;

(b) means adapted for guiding a tool along a predetermined arcuate path for controlled shaping of a patellar groove in the selected portion of the femur exposed through the opening; and (c) a replaceable insert covering the opening and having a distal surface for fully articulating the external surface of the bracket with a proximal aspect of the tibia during interoperative trial reduction of the knee joint, without prior removal of the bracket from the resected bone following shaping of the patellar groove.

2. The trial implant of claim 1 wherein the means described in (b) further comprises a track extending along a side of the opening and adapted to contact the tool as the tool moves along the track.

3. The trial implant of claim 2 wherein the track further comprises a pair of rails formed along opposed sides of the opening.

4. The trial implant of claim 1 further comprising means for reversibly interlocking the insert with the guide means of (b).

5. A method of implanting a condylar prosthesis onto the distal aspect of a femur comprising the steps of:

(a) resecting the distal aspect of the femur to receive a trial implant thereon;

(b) providing a trial implant including, in combination, a bracket defining a modular structure with an internal surface adapted to be seated on the distal aspect of the femur and an external surface formed with a shape partially resembling the normal distal condyle, including an elongated central opening appointed to expose a selected portion of the anterior distal resected surface of the femur to a shaping tool and means for guiding the tool along a predetermined arcuate path, and an insert which is replaceable to cover the opening and allow full articulation of the external surface of the bracket with the proximal aspect of the tibia;

(c) moving the shaping tool along the guide means, cutting or abrading a patellar groove in the selected portion of the femur exposed through the opening;

(d) placing the insert securely over the opening; and (e) performing a trial reduction of the knee joint, without removing the modular bracket.

* * * * *